United States Patent [19]

Rivetti et al.

[11] Patent Number: 5,527,943
[45] Date of Patent: Jun. 18, 1996

[54] METHOD FOR REMOVING ACID AND SALINE CONTAMINANTS FROM A GASEOUS STREAM LEAVING A DIMETHYLCARBONATE SYNTHESIS REACTOR

[75] Inventors: Franco Rivetti; Ugo Romano, both of Milan; Guido Garone, Como; Maurizio Ghirardini, Milan, all of Italy

[73] Assignee: Enichem Synthesis S.p.A., Palermo, Italy

[21] Appl. No.: 272,229

[22] Filed: Jul. 8, 1994

[30] Foreign Application Priority Data

Jul. 15, 1993 [IT] Italy ................... MI93A1564

[51] Int. Cl.⁶ ................................. C07C 69/96
[52] U.S. Cl. ............................. 558/277; 558/260
[58] Field of Search ....................... 558/260, 277

[56] References Cited

FOREIGN PATENT DOCUMENTS 0534545  3/1993  European Pat. Off. .

Primary Examiner—José G. Dees
Assistant Examiner—Dwayne C. Jones
Attorney, Agent, or Firm—Oblon, Spivak, McClelland, Maier & Neustadt

[57] ABSTRACT

A method is described enabling HCl and possible entrained CuCl particulate to be removed from a gas-vapor stream leaving a dimethylcarbonate synthesis reactor. The contaminant removal is effected by one of the process fluids used in a small quantity.

8 Claims, 3 Drawing Sheets

METHOD FOR REMOVING ACID AND SALINE CONTAMINANTS FROM A GASEOUS STREAM LEAVING A DIMETHYLCARBONATE SYNTHESIS REACTOR

BACKGROUND OF THE INVENTION

This invention relates to a method for removing acid or saline contaminants from a gas-vapour mixture leaving a dimethylcarbonate synthesis reactor.

Dimethylcarbonate (hereinafter known as DMC) is a widely used chemical product of great versatility, employed as such as a solvent or as a fuel additive; DMC is also an important intermediate in the synthesis of alkyl or aryl carbonates, which are used as synthetic lubricants, solvents, monomers for polymeric materials and for the preparation of isocyanates, urethanes, ureas and polycarbonates.

The path currently most followed for producing DMC is based on oxidative carbonylation of methanol, in particular in the presence of CuCl as catalyst, in accordance with the reaction:

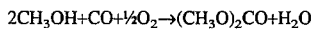

$$2CH_3OH + CO + \tfrac{1}{2}O_2 \rightarrow (CH_3O)_2CO + H_2O$$

The preparation of DMC in accordance with this reaction is described for example in U.S. Pat. Nos. 4,218,391 and 4,318,862 in the name of the present applicant.

Improvements to the processes described in said U.S. patents are introduced in European patent applications EP-A-460,732 and EP-A-460,735 in the name of the present applicant, the content of which forms part of the present application as reference. These applications describe a continuous DMC synthesis process in which the reaction products are removed from the reactor in the vapour phase. Leaving the reactor in this process there is a saturated gaseous stream containing vapour of the water/methanol/DMC system plus unreacted CO and $O_2$, $CO_2$ deriving from a second reaction and possibly inert gases present in the feed to the reactor ($H_2$, Ar, $N_2$ etc.). This gas-vapour mixture is passed through a condenser which separates a water/methanol/DMC liquid mixture from the uncondensable gases, which are largely recycled to the reaction. The water/methanol/DMC liquid stream is then fed to the separation section which by distillation and liquid-liquid separation recovers the DMC and the water produced, and recycles the unreacted methanol to synthesis.

This process has however the drawback that the gaseous stream leaving the reactor is contaminated with a small quantity of hydrochloric acid of generally between 30 and 300 ppm by volume, which is released from the catalyst used in the reaction. In addition to HCl, the gaseous stream leaving the reactor can also contain small quantities of halogenated copper salts deriving from catalyst entrainment in the form of particulate and/or droplets of micron dimensions. The amount of copper transferred in this manner is generally between about 1 and 20 mg Cu/Nm$^3$.

The presence of chloride ions and possible copper ions results in considerable problems in those plant sections downstream of the reactor. The stage in which the gaseous mixture leaving the reactor is condensed is particularly critical. In this respect, it is not possible to condense this gaseous mixture in a conventional steel condenser because of resultant serious equipment corrosion by the HCl. Again, the use of corrosion resistant materials such as enamelled steel is technically unfit because of the fact that these materials generally have a low heat transfer coefficient, so that a condenser of prohibitive dimensions would be required for condensing a large acid gas throughput, taking into account the high price of such materials. Operating under conditions of complete condensation using corrosion resistant plants could represent an acceptable solution to the aforesaid problems if operating in low production plants with equipment of small dimensions. However even in this case there would still be the drawback of having to process the entire condensed liquid mass, which before being fed to the product recovery section would have to be neutralized and finally separated from the salts formed by neutralizing the acid.

SUMMARY OF THE INVENTION

An object of the present invention is to overcome the drawbacks of processes of the known art.

A more particular object of the present invention is to provide a method which enables the HCl and copper salts to be eliminated or nearly eliminated from the gaseous stream leaving the reactor, in a process stage conducted in small dimension equipment which reduces the concentration of said contaminants to values such as to enable equipment constructed of conventional materials to be used for the subsequent process stages.

These and further objects are attained according to the invention by a method for purifying from HCl and possibly copper salts a gas-vapour stream leaving a DMC synthesis reactor, consisting of bringing said stream into contact with a fluid of the synthesis process at a temperature substantially equal to or less than the temperature of the stream itself, and subsequently condensing the vapour contained in the purified gas-vapour stream.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
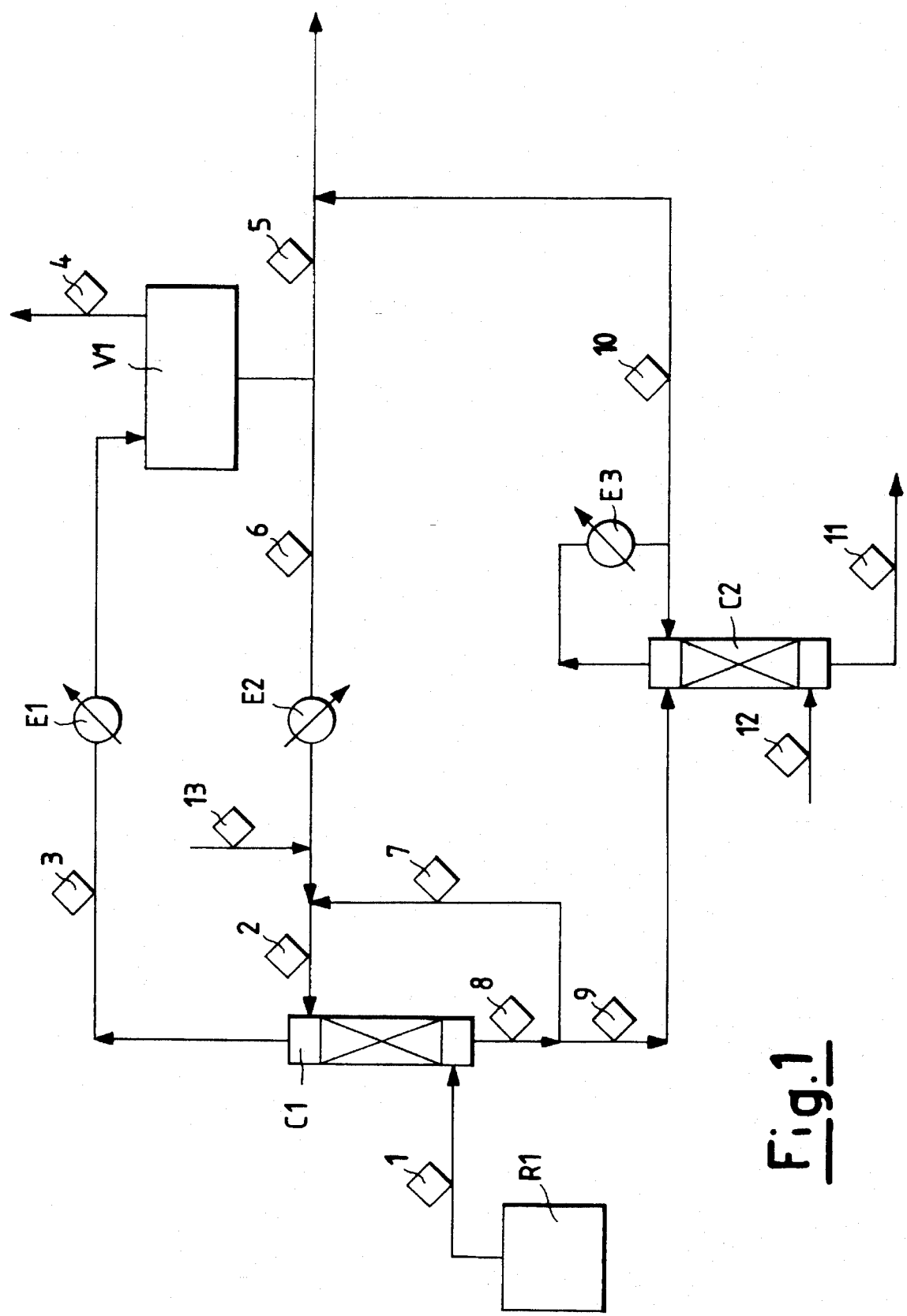
FIG. 1 shows a process stream using a 5 HETP packed column and a 15 HETP distillation column, in which a stream exiting the bottom of the 5 HETP packed column is recycled to the top of the same column.

According to a preferred embodiment of the present invention, the temperature of the process fluid used for purifying the gas-vapour stream is equal to the temperature of the stream itself, and the throughput of said process fluid is maintained at the minimum value compatible with the effectiveness of the method, generally between 0.1 and 1 kg of liquid mixture per Nm$^3$ of gaseous stream to be treated.

The gas-vapour stream to be separated in the first stage of the method can derive from any industrial DMC production process known in the art in which the products are removed as a gaseous stream. Particularly convenient for this purpose is the process described in the cited European patent applications EP-A-460,732 and EP-A-460,735.

The removal of HCl and possible copper salts can be implemented in any known equipment used in the art for bringing different fluids into intimate contact, such as packed or plate columns, spray chambers, cyclone or ejector separators, etc. The use of multi-stage countercurrent systems (packed or plate columns) is preferred because of their greater versatility when operating conditions vary.

Contaminant removal within a chamber of the aforesaid type is effected by a liquid stream consisting of one of the process fluids or a mixture of them. It is particularly convenient to operate with a liquid stream in the form of a water/methanol/DMC mixture, ie the mixture which is obtained by condensing the purified gaseous stream.

Generally, the gas-vapour mixture is treated at a temperature essentially equal to or less than the temperature of the mixture itself, under conditions such that the vapour arriving from the reactor does not condense or only partly condenses.

The operating conditions are preferably such that the gaseous mixture from the reactor does not condense or condenses only to a negligible extent. This condition is achieved mainly by controlling the temperature of the liquid stream used for removing the contaminants, by maintaining said liquid stream at a temperature equal or essentially equal to that of the gaseous stream to be purified. This gaseous stream is at the reactor temperature, generally between 120° and 150° C. Conveniently, the minimum operating temperature is about 2° C. less than the temperature of the gaseous stream to be purified. The highest temperature is generally that of the gaseous stream to be purified; at higher temperatures the undesirable phenomenon of partial evaporation of the liquid stream could occur. In addition, operating with a liquid mixture at a temperature higher than the gaseous mixture would imply higher operating costs without any process advantage.

The operating pressure under which the contaminants are removed is not critical, being for example between atmospheric pressure and the pressure of the synthesis reactor. For simplicity, it is preferable to operate at a pressure substantially equal to the reactor pressure, which is normally between 15 and 40 bar. The throughput of the liquid stream used is maintained at the lowest possible value compatible with the effectiveness of the removal process. This throughput can generally vary between about 0.1 and 1 kg per $Nm^3$ of the gas-vapour mixture to be purified. As stated, the liquid stream used to remove the contaminants is preferably obtained by withdrawing it from the line carrying the water/methanol/DMC mixture to the distillation stage. In a further embodiment of the method of the present invention, said withdrawal can be reduced by recycling from the bottom to the top of the removal chamber, so increasing the quantity fed to distillation and hence to product recovery. In this operating method, the liquid mixture leaving the bottom of the removal chamber is fed to the top of the chamber, adding to it at each cycle a small quantity of the "fresh" mixture withdrawn downstream of the condenser. Under these conditions the quantity of "fresh" mixture used is reduced to the order of 0.01–0.05 kg per $Nm^3$ of gaseous mixture to be treated.

Optionally, an HCl neutralization agent, which can be an organic or inorganic base, can be dissolved in this liquid stream. Particularly convenient is the use of sodium or potassium hydroxides, carbonates or bicarbonates. In this case the HCl is converted into the corresponding sodium or potassium chloride. Any copper present in chloride form is converted into hydroxide or hydroxychloride. If said neutralizing agent is used, its concentration is such that under operating conditions the quantity ratio of neutralizing agent to HCl (and the possible copper salt) is stoichiometric at 1:1 or a slight 5–10% excess of neutralizing agent. A larger excess of neutralizing agent is possible but not convenient, and could result in DMC hydrolysis, with consequent loss of product.

Recovery can be effected on the liquid stream leaving the bottom of the removal chamber by stripping the organic components, to obtain DMC to be added to the distillation product, and methanol to be fed to synthesis. During this operation an aqueous solution of HCl or its salts and possibly copper salts is also obtained. In a further embodiment of the method of the present invention the HCl solution can be recycled, after possible concentration, to the DMC synthesis reactor for regeneration of the CuCl catalyst, in accordance with the method described in Italian patent MI/91-A-02529, the content of which forms part of the present patent application as reference.

The purified gas-vapour mixture is then fed to condensation and distillation, conducted by methods known to the art. For all operations downstream of the purification, steel equipment of traditional type is used.

As stated, the process of the present invention offers various advantages, in particular the fact that by operating in the described manner the contaminants are separated using small volumes of scrubbing liquid, so that the subsequent operations involved in eliminating the contaminants are effected on small volumes and not on the whole liquid mass which would be obtained by completely condensing the vapour of the gaseous mixture leaving the reactor.

Some examples of possible embodiments of the process of the present invention are given hereinafter in order to provide a clearer description of the process, but are not to be considered as in any way limiting the scope of the invention.

EXAMPLE 1

A gas-vapour stream consisting of 200 Nl/h of CO and 235 g/h of a vapour mixture of the following composition by weight:

| | |
|---|---|
| $CH_3OH$ | 62.7% |
| DMC | 30.4% |
| $H_2O$ | 6.8% |
| HCl | 0.1% (equivalent to 1000 ppm) | was fed at a temperature of 52° C. to the bottom of a plate column of 2.54 cm inner diameter fitted with 10 Oldershaw plates and operating at atmospheric pressure.

130 g/h of a solution of $KHCO_3$ in a mixture of the following composition by weight:

| | |
|---|---|
| $CH_3OH$ | 64.3% |
| DMC | 18.7% |
| $H_2O$ | 17.0% | were fed to the top of the column at a temperature of 52° C.

The weight concentration of the $KHCO_3$ solution is 15 g/kg, which corresponds to saturation concentration in the given mixture at the given temperature.

After counter-current contact between the two streams within the column, a gas-vapour stream was obtained from the top of the column which, after condensation by cooling to −10° C., provided 250 g/h of a liquid mixture of the following composition by weight:

| | |
|---|---|
| CH$_3$OH | 62.6% |
| DMC | 32.6% |
| H$_2$O | 4.8% |
| HCl | 3 ppm |

A liquid stream containing 0.41 wt. % of KCl and the excess of KHCO$_3$ was discharged from the bottom of the column.

EXAMPLE 2

The test of Example 1 was repeated but varying the HCl concentration in the gas-vapour stream fed to the bottom of the column and the throughput of the removal solution, these values being respectively 1500 ppm of HCl (0.15 wt. %) in the gas-vapour stream to be purified and 60 g/h of fed KHCO$_3$ solution. 4 ppm of chloride ions were found in the liquid mixture obtained by condensing the gaseous stream leaving the top of the reactor.

EXAMPLE 3

A gas-vapour stream consisting of 360 Nl/h of CO and 260 g/h of a vapour mixture of the following composition by weight:

| | |
|---|---|
| CH$_3$OH | 58.3% |
| DMC | 34.7% |
| H$_2$O | 7.0% |
| HCl | 0.3% (equivalent to 3000 ppm) | was fed at atmospheric pressure and a temperature of 48° C. to the apparatus of Example 1.

60 g/h of liquid mixture of the following composition by weight:

| | |
|---|---|
| CH$_3$OH | 61.9% |
| DMC | 31.9% |
| H$_2$O | 6.2% | were fed to the top of the column at a temperature of 48° C.

After condensation at −10° C., the gas-vapour mixture leaving the top of the column provided 290 g/h of a liquid mixture of the following composition by weight:

| | |
|---|---|
| CH$_3$OH | 58.6% |
| DMC | 36.5% |
| H$_2$O | 4.9% |
| HCl | 6 ppm |

A liquid stream (30 g/h) containing 2.57 wt. % of HCl was discharged from the bottom of the column.

EXAMPLE 4

In the description of this example, reference is made to the accompanying FIG. 1. In the text, the numbers in parentheses refer to the streams indicated in the figure.

A DMC synthesis reactor R1 operating at a temperature of 130° C. and a pressure of 24 bar produces a continuous gas-vapour stream (1) of the following composition by volume:

| | | |
|---|---|---|
| CO | 43.8% | |
| CO$_2$ | 6.7% | |
| O$_2$ | 0.4% | |
| Uncondensable inert gases | 16.8% | |
| CH$_3$OH | 25.0% | |
| DMC | 4.8% | |
| H$_2$O | 2.1% | |
| Other organics | 0.4% | |
| HCl | 125 | ppm by volume |
| Cu | 8.5 | mg/Nm$^3$ |

4000 Nm$^3$/h of stream (1) are fed to the bottom of an enamelled packed column C1 having a height of about 5 theoretical plates. 830 kg/h of a liquid stream (2) are fed to the top of the column, the stream (2) being maintained at a temperature of 130° C. and having a composition by weight, determined by gas chromatography, as follows:

| | | |
|---|---|---|
| CH$_3$OH | 58.8% | |
| DMC | 33.2% | |
| H$_2$O | 6.7% | |
| Other organics | 1.2% | |
| KHCO$_3$ | 0.48% | |
| KCl | 1.35% | |
| Cu | 270 | ppm by weight |

4000 Nm$^3$/h of a gas-vapour stream (3) of the following composition by volume:

| | | |
|---|---|---|
| CO | 44.1% | |
| CO$_2$ | 6.7% | |
| O$_2$ | 0.4% | |
| Uncondensable inert gases | 17.0% | |
| CH$_3$OH | 24.7% | |
| DMC | 4.8% | |
| H$_2$O | 1.9% | |
| Other organics | 0.4% | |
| HCl | 1 | ppm |
| Cu | <0.1 | mg/Nm$^3$ | are withdrawn from the top of the column.

The stream (3) is fed to a shell-and-tube heat exchanger E1 of AISI 304L steel, in which the gas-vapour mixture is condensed at 60° C. and 24 bar. The condensate is collected in the tank V1, which is under the same temperature and pressure conditions as from the top of V1 there being extracted 2700 Nm$^3$/h of a stream of uncondensables (4) of the following composition by volume:

| | |
|---|---|
| CO | 63.7% |
| CO$_2$ | 9.3% |
| O$_2$ | 0.5% |
| Uncondensable inert gases | 24.5% |
| Organics | 2.0% |

This gas stream is partly bled off and partly recycled to synthesis. The liquid mixture which collects in V1 has the following composition by weight:

| | |
|---|---|
| CH$_3$OH | 62.0% |
| DMC | 34.0% |
| H$_2$O | 2.8% |
| Others | 1.2% |

2060 kg/h of a liquid stream (5) are extracted from the bottom of V1 and fed to the separation section for recovering DMC and recycling unreacted methanol. A part of the condensate, the stream (6), is heated to 130° C. in the heat exchanger E2, and KHCO$_3$ [stream (13)] is added to obtain a solution containing 2.25 wt. % of this base. 110 kg/h of the stream (6) are fed to the top of the column C1 together with the stream (7) obtained by recycling from the bottom of the column C1.

The stream (8), leaving the bottom of the column C1 at a rate of 830 kg/h, has the following composition by weight:

| | |
|---|---|
| $CH_3OH$ | 58.3% |
| DMC | 33.3% |
| $H_2O$ | 7.3% |
| Others | 1.1% |
| KCl | 1.50% |
| $KHCO_3$ | 0.22% |
| Cu | 310 ppm |

A part of the stream (8), equal to 720 kg/h, is recycled to the top of the column [stream (7)], the remaining 110 kg/h of stream (8) being withdrawn and fed to an enamelled distillation column C2 of height equivalent to 15 theoretical plates, operating at atmospheric pressure, and in which the heat is provided by direct steam (12) at 150° C. and 5 ata at a rate of 60 kg/h.

115 kg/h of a stream (10) of the following composition by weight:

| | |
|---|---|
| $CH_3OH$ | 55.9% |
| DMC | 31.9% |
| $H_2O$ | 11.2% |
| Others | 1.0% | are extracted from the top of the column C2 at a temperature of 85° C.

This stream together with the stream (5) is fed to the separation section.

57 kg/h of an aqueous solution (11) containing 3 wt. % of KCl, 0.45 wt. % of $KHCO_3$ and 600 ppm by weight of copper are discharged at a temperature of 105° C. from the bottom of the column C2.

EXAMPLE 5

Figure 2:
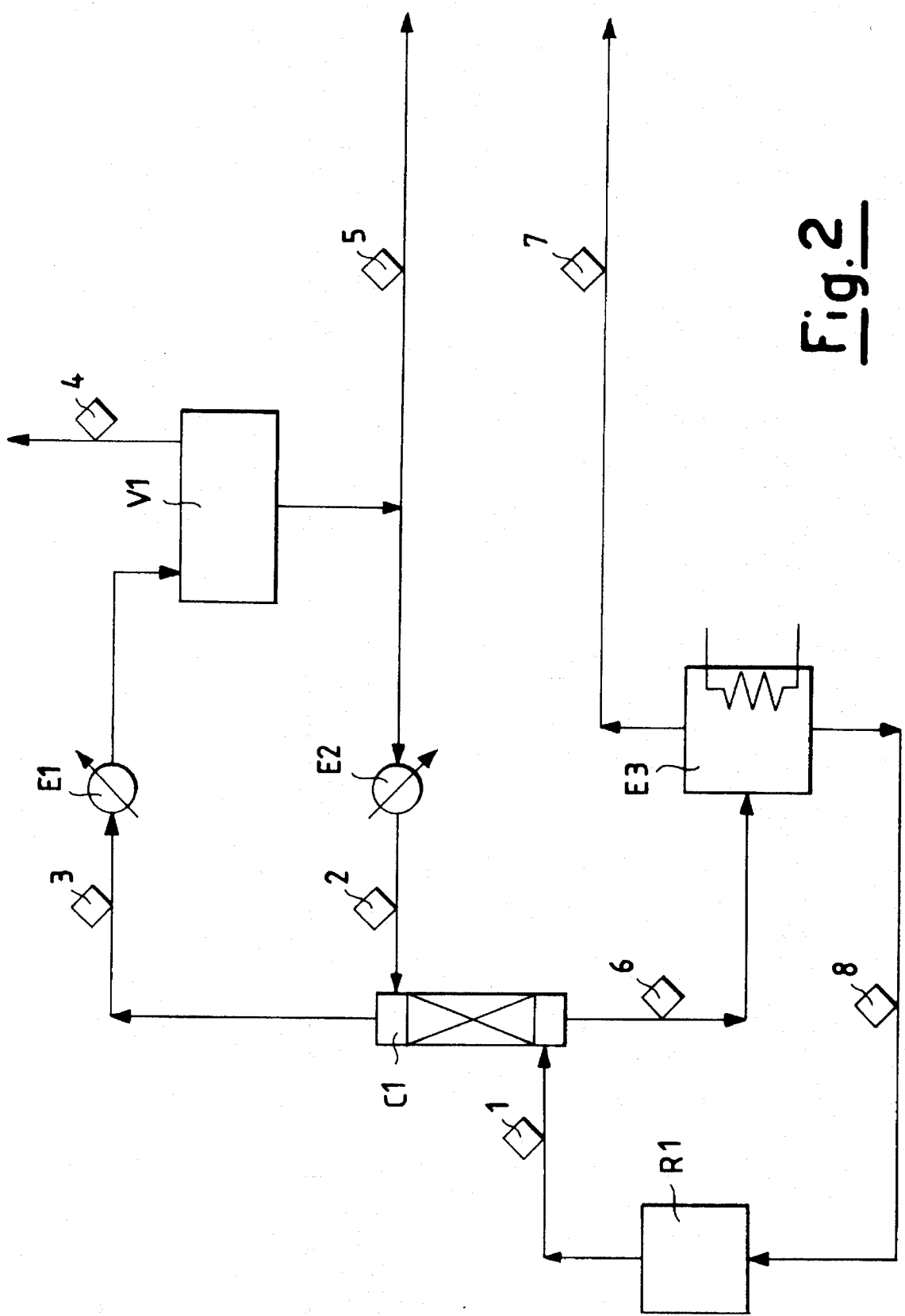
FIG. 2 shows a process stream using a 5 HETP packed column and a shell and tube evaporator, in which a stream exiting the bottom of the evaporator is recycled to the DMC reactor.

In the description of this example, reference is made to the accompanying FIG. 2. In the text, the numbers in parentheses refer to the streams indicated in the figure.

CO, $O_2$ and $CH_3OH$ are reacted in a DMC synthesis reactor R1 in the presence of CuCl as catalyst at a temperature of 130° C. and a pressure of 24 bar. The gas-vapour stream (1) leaving the reactor has the following composition by volume:

| | |
|---|---|
| CO | 43.8% |
| $CO_2$ | 6.7% |
| $O_2$ | 0.4% |
| Uncondensable inert gases | 16.8% |
| $CH_3OH$ | 25.0% |
| DMC | 4.8% |
| $H_2O$ | 2.1% |
| Other organics | 0.4% |
| HCl | 125 ppm by volume |
| Cu | 8.5 mg/$Nm^3$ |

This stream is fed to the bottom of an enamelled packed column Cl having a height equivalent to about 5 theoretical plates. 830 kg/h of a liquid stream (2) having the following composition by weight:

| | |
|---|---|
| $CH_3OH$ | 61.9% |

-continued

| | |
|---|---|
| DMC | 33.3% |
| $H_2O$ | 3.3% |
| Other organics | 1.5% | are fed to the top of the column C1 at a temperature of 130° C.

4000 $Nm^3$/h of a gas-vapour stream (3) of the following composition by volume:

| | |
|---|---|
| CO | 44.1% |
| $CO_2$ | 6.7% |
| $O_2$ | 0.4% |
| Uncondensable inert gases | 17.0% |
| $CH_3OH$ | 24.7% |
| DMC | 4.8% |
| $H_2O$ | 1.9% |
| Other organics | 0.4% |
| HCl | 1 ppm |
| Cu | <0.1 mg/$Nm^3$ | are extracted from the top of the column C1.

The stream (3) is fed to a shell-and-tube heat exchanger E1 of AISI 304L steel, in which the gas-vapour mixture is condensed at 60° C. and 24 bar. The condensed compounds are collected in the tank V1, which is under the same temperature and pressure conditions as E1, from the top of V1 there being extracted 2700 $Nm^3$/h of a stream of uncondensables (4) of the following composition by volume:

| | |
|---|---|
| CO | 63.7% |
| $CO_2$ | 9.3% |
| $O_2$ | 0.5% |
| Uncondensable inert gases | 24.5% |
| Organics | 2.0% |

This gas stream is partly bled off and partly recycled to synthesis.

The liquid mixture which collects in V1 has the following composition by weight:

| | |
|---|---|
| $CH_3OH$ | 61.9% |
| DMC | 33.3% |
| $H_2O$ | 3.3% |
| Others | 1.5% |

1340 kg/h of a liquid stream (5) are extracted from the bottom of V1 and fed to the separation section for recovering DMC and recycling unreacted methanol. A part of the condensate which collects in V1 forms the stream (2), which is heated to 130° C. in the heat exchanger E2 and fed to the top of the column C1. 830 kg/h of a stream (6) having the following composition by weight:

| | |
|---|---|
| $CH_3OH$ | 61.8% |
| DMC | 33.3% |
| $H_2O$ | 3.4% |
| Other organics | 1.5% |
| HCl | 0.1% |
| Cu | 40 ppm by weight | are extracted from the bottom of the column C1.

The stream (6) is fed to a shell-and-tube evaporator E3 of Hastelloy C operating at atmospheric pressure. By vaporization, 790 kg/h of a stream (7) leaves E3 at a temperature of 70° C. and has the following composition by volume:

| | |
|---|---|
| $CH_3OH$ | 62.2% |
| DMC | 33.3% |
| $H_2O$ | 2.9% |
| Other organics | 1.6% |
| HCl | 5 ppm |

The stream (7) is combined with the stream (5) and fed to the separation section for product recovery.

From the bottom of the evaporator E3, 40 kg/h of a stream (8) are obtained with the following composition by weight:

| | |
|---|---|
| $CH_3OH$ | 58.3% |
| DMC | 33.3% |
| $H_2O$ | 7.4% |
| Other organics | 1.0% |
| HCl | 2.05% |

The stream (8) is recycled to the reactor R1.

EXAMPLE 6

Figure 3:
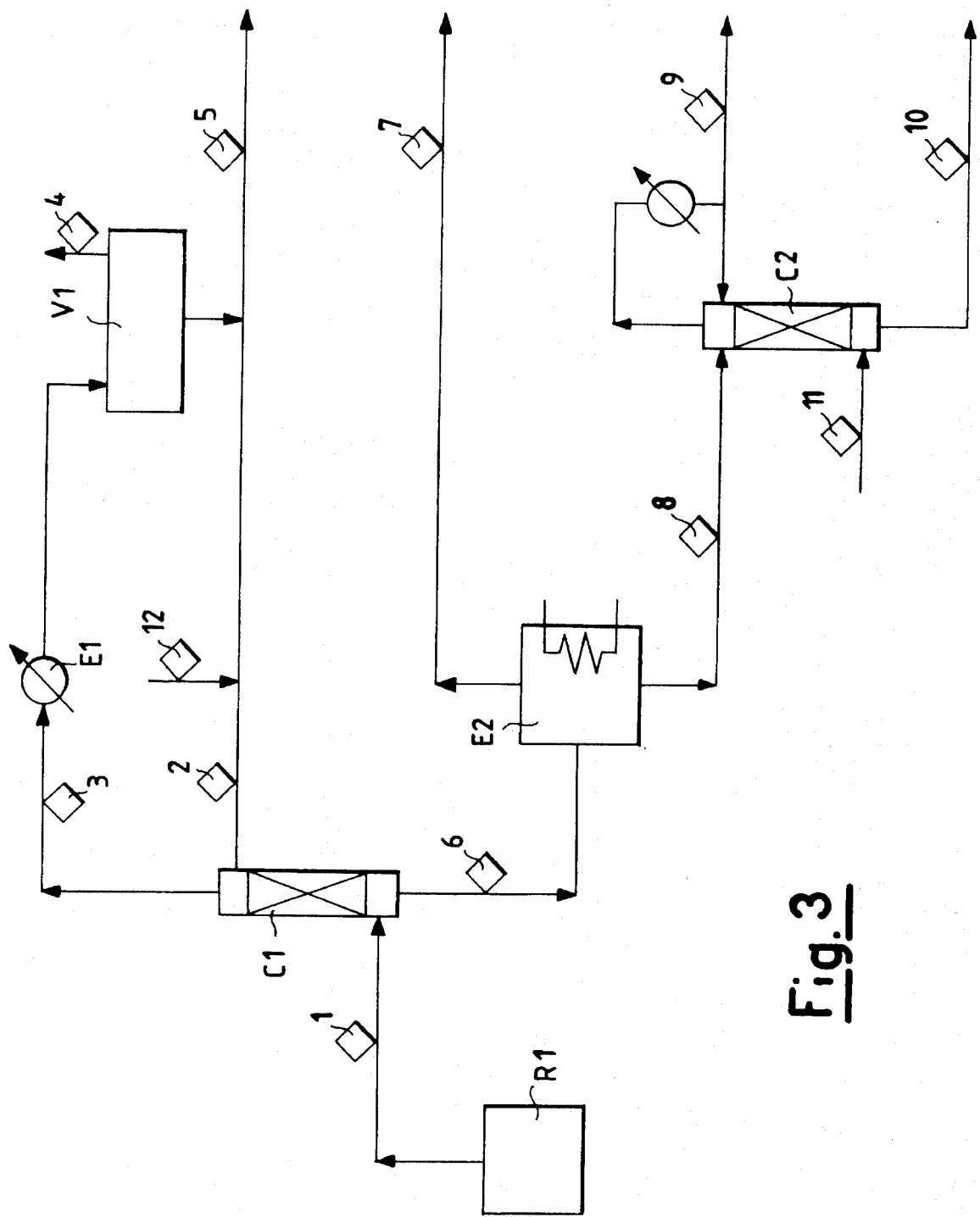
FIG. 3 shows a process stream using a 5 HETP packed column, a 15 HETP distillation column and a shell and tube evaporator.

In the description of this example, reference is made to the accompanying FIG. 3. In the text, the numbers in parentheses refer to the streams indicated in the figure.

$CH_3OH$, CO and $O_2$ are continuously reacted in a DMC synthesis reactor R1 in the presence of CuCl as catalyst, operating at a temperature of 130° C. and a pressure of 24 bar. The gas-vapour stream (1) leaving the reactor has the following composition by volume:

| | |
|---|---|
| CO | 43.8% |
| $CO_2$ | 6.7% |
| $O_2$ | 0.4% |
| Uncondensable inert gases | 16.8% |
| $CH_3OH$ | 25.0% |
| DMC | 4.8% |
| $H_2O$ | 2.1% |
| Other organics | 0.4% |
| HCl | 125 ppm by volume |
| Cu | 8.5 mg/Nm$^3$ |

4000 Nm$^3$/h of this gas-vapour stream are fed to the bottom of an enamelled packed column C1 having a height equivalent to about 5 theoretical plates.

830 kg/h of a liquid stream (2) having the following composition by weight:

| | |
|---|---|
| $CH_3OH$ | 62.0% |
| DMC | 33.4% |
| $H_2O$ | 3.1% |
| Other organics | 1.5% |
| NaOH | 0.12% | are fed to the top of the column C1 at a temperature of 65° C.

3850 Nm$^3$/h of a gas-vapour stream (3) of the following composition by volume:

| | |
|---|---|
| CO | 44.8% |
| $CO_2$ | 6.9% |
| $O_2$ | 0.4% |
| Uncondensable inert gases | 17.2% |
| $CH_3OH$ | 23.7% |
| DMC | 4.6% |
| $H_2O$ | 2.0% |
| Other organics | 0.4% |
| HCl | 1 ppm by volume |
| Cu | <0.1 mg/Nm$^3$ | are extracted from the top of the column C1.

The gas-vapour mixture leaving the column C1 is condensed in the shell-and-tube heat exchanger E1 of AISI 304L steel, at a temperature of 65° C. and a pressure of 24 bar.

The organic condensed products are collected in the tank V1, operating under the same temperature and pressure conditions as E1, the stream (4) containing the uncondensables being partly recycled to the reaction and partly bled off. This stream, with a flow rate of 2700 Nm$^3$/h, has the following composition by volume:

| | |
|---|---|
| CO | 63.7% |
| $CO_2$ | 9.3% |
| $O_2$ | 0.5% |
| Uncondensable inert gases | 24.5% |
| Organics | 2.0% |

1240 kg/h of a liquid stream (5) having the following composition by weight:

| | |
|---|---|
| $CH_3OH$ | 62.0% |
| DMC | 33.4% |
| $H_2O$ | 3.1% |
| Others | 1.5% | are extracted from the bottom of V1.

This liquid stream is fed to the separation section for product recovery and recycling unreacted methanol. 0.12 wt. % of NaOH [stream (12)] is added to a part of the condensate, to form the stream (2) which is fed to the top of the column C1. The stream (6) leaving the bottom of the column C1 has a flow rate of 990 kg/h, with the following composition by weight:

| | |
|---|---|
| $CH_3OH$ | 61.8% |
| DMC | 33.4% |
| $H_2O$ | 3.3% |
| Others | 1.5% |
| NaCl | 0.13% |
| NaOH | 0.01% |
| Cu | 35 ppm |

This stream is fed to a shell-and-tube evaporator E2 of Hastelloy C operating at atmospheric pressure, by which 940 kg/h of a stream (7) are evaporated at 70° C. and having the following composition by volume:

| | |
|---|---|
| $CH_3OH$ | 62.1% |
| DMC | 33.3% |
| $H_2O$ | 3.0% |
| Others | 1.6% |

This stream is combined with the stream (5) and fed to the separation section.

From the bottom of the evaporator E2, 50 kg/h of a liquid stream (8) are extracted with the following composition by weight:

| | |
|---|---|
| $CH_3OH$ | 56.7% |
| DMC | 32.4% |
| $H_2O$ | 7.0% |
| Other organics | 1.0% |
| NaCl | 2.6% |

-continued

| | |
|---|---|
| NaOH | 0.2% |
| Cu | 700 ppm |

This stream is fed to an enamelled distillation column C2 of height equivalent to 15 theoretical plates, operating at atmospheric pressure. This column is heated by direct steam at 150° C. (5 ata) at a rate of 30 kg/h [stream (11)].

50 kg/h of a stream (9) of the following composition by weight:

| | |
|---|---|
| $CH_3OH$ | 55.9% |
| DMC | 31.9% |
| $H_2O$ | 11.2% |
| Others | 1.0% | are extracted from the top of the column C2 at a temperature of 85° C.

This stream is combined with the streams (5) and (7) and fed to the separation section.

30 kg/h of an aqueous solution [stream (10)] of the following composition by weight:

| | |
|---|---|
| $H_2O$ | 95.3% |
| NaCl | 4.3% |
| NaOH | 0.3% |
| Cu | 0.1% | are discharged at a temperature of 105° C. from the bottom of the column C2.

We claim:

1. A method for removing HCl and possibly copper salts from a gas-vapour stream leaving a DMC synthesis reactor, consisting of bringing said stream into contact with a fluid of the synthesis process at a temperature essentially equal to or less than the temperature of the stream itself, and condensing the vapour contained in the purified gas-vapour stream.

2. A method as claimed in claim 1, wherein the process fluid used for removing HCl and copper salts is at the same temperature as the gas-vapour stream to be treated.

3. A method as claimed in claim 1, wherein the quantity of liquid used for removal is between 0.1 and 1 kg of liquid mixture per $Nm^3$ of gaseous stream to be purified.

4. A method as claimed in claim 1, wherein the liquid used for removing HCl and possible copper salts is obtained partly by withdrawal downstream of the condenser and partly by recycling the actual liquid mixture leaving the removal chamber.

5. A method as claimed in claim 1, wherein an organic or inorganic base is added to the liquid used for removing HCl and possible copper salts.

6. A method as claimed in claim 5, wherein the base is sodium or potassium hydroxide, carbonate or bicarbonate.

7. A method as claimed in claim 5, wherein the base is added to the removal liquid mixture in a quantity such that its ratio to the sum of HCl plus possible copper salts to be removed varies between stoichiometric 1:1 and 1.1:1.

8. A method for removing HCl and possibly copper salts from a gas-vapour stream leaving a DMC synthesis reactor, consisting of bringing said stream into contact with a fluid of the synthesis process at a temperature essentially equal to or less than the temperature of the stream itself, and condensing the vapour contained in the purified gas-vapour stream, wherein the removal of HCl and copper salts is effected by a water/methanol/DMC liquid mixture obtained by condensing the gas-vapour mixture leaving the removal chamber.

* * * * *